United States Patent
Nguyen (10) Patent No.: US 12,398,412 B2
(45) Date of Patent: Aug. 26, 2025

(54) REGULATION OF POLYMERASE USING COFACTOR OXIDATION STATES

(71) Applicant: MICROSOFT TECHNOLOGY LICENSING, LLC, Redmond, WA (US)

(72) Inventor: Bichlien Hoang Nguyen, Seattle, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 0 days.

(21) Appl. No.: 18/221,364

(22) Filed: Jul. 12, 2023

(65) Prior Publication Data
US 2023/0348946 A1    Nov. 2, 2023

Related U.S. Application Data

(62) Division of application No. 16/543,433, filed on Aug. 16, 2019, now Pat. No. 11,773,422.

(51) Int. Cl.
*C12Q 1/6844* (2018.01)
*B01J 19/00* (2006.01)
(Continued)

(52) U.S. Cl.
CPC ............ *C12P 19/36* (2013.01); *B01J 19/0046* (2013.01); *C12Q 1/6874* (2013.01);
(Continued)

(58) Field of Classification Search
CPC .................... B01J 2219/00713; C12Q 1/6844
See application file for complete search history.

(56) References Cited

U.S. PATENT DOCUMENTS 5,298,414 A * 3/1994 Bruce ................... C12Q 1/004
435/26
7,056,666 B2   6/2006 Dower
(Continued)

FOREIGN PATENT DOCUMENTS

WO        9726002 A1   7/1997
WO     2008051454 A1   5/2008
(Continued)

OTHER PUBLICATIONS

Riguero, et al., "Immobilized Metal Affinity Chromatography Optimization for Poly-histidine Tagged Proteins", In Journal of Chromatography A, vol. 1629, Aug. 21, 2020, pp. 1-19.
(Continued)

*Primary Examiner* — Paul S Hyun
(74) *Attorney, Agent, or Firm* — Benjamin Keim; Newport IP, LLC (57) ABSTRACT

Polynucleotide synthesis performed with a template independent polymerase such as terminal deoxynucleotidyl transferase (TdT) is regulated by controlling the oxidation state of a metal cofactor. The oxidation state of the metal cofactor is changed to +2, thus activating the polymerase, by applying a voltage with electrodes or by introducing a chemical redox reagent. Addressable polynucleotide synthesis creates polynucleotides with different arbitrary sequences through use of spatial control of cofactor oxidation states to add nucleotides only at selected locations on an array. Control of metal oxidation states is regulated by selective activation of a microelectrode array, controlled addition of redox reagents to specific locations on the array, or controlled activation of photocatalysts at specific locations on the array. Scavengers in solution prevent cofactors distant from the selected locations from catalyzing poly-
(Continued)

merase activity and thereby maintain the localized effect of polymerase activation.

20 Claims, 5 Drawing Sheets

(51) Int. Cl.
    *C12P 19/36*     (2006.01)
    *C12Q 1/6874*     (2018.01)
    *C12P 19/34*     (2006.01)
(52) U.S. Cl.
    CPC .................. *C12Y 207/07031* (2013.01); *B01J 2219/00711* (2013.01); *B01J 2219/00713* (2013.01); *C12P 19/34* (2013.01); *C12Y 207/07006* (2013.01)

(56) References Cited

U.S. PATENT DOCUMENTS

| | | | |
|---|---|---|---|
| 11,414,776 B2 * | 8/2022 | Lin | ........................... C25F 3/12 |
| 11,702,683 B2 | 7/2023 | Nguyen | |
| 2011/0092384 A1 | 4/2011 | Kwon | |
| 2015/0203887 A1 | 7/2015 | Lazinski et al. | |
| 2019/0113521 A1 | 4/2019 | Moola | |
| 2020/0362394 A1 | 11/2020 | Gawad et al. | |
| 2024/0018511 A1 | 1/2024 | Nguyen | |
| 2024/0408564 A1 | 12/2024 | Nguyen | |

FOREIGN PATENT DOCUMENTS

| | | | |
|---|---|---|---|
| WO | 2015113828 A1 | 8/2015 | |
| WO | 2017165438 A1 | 9/2017 | |
| WO | WO-2018119253 A1 * | 6/2018 | ........... C12N 9/1241 |
| WO | 2018121678 A1 | 7/2018 | |
| WO | 20230154712 A1 | 8/2023 | |

OTHER PUBLICATIONS

Ghindilis, et al., "Enzyme-Catalyzed Direct Electron Transfer: Fundamentals and Analytical Applications", In journal of Electroanalysis, vol. 9, Issue 9, Feb. 10, 1997, pp. 661-674.
Kuznetsova, et al., "Insight into the Mechanism of DNA Synthesis by Human Terminal Deoxynucleotidyltransferase", In Journal of Life Science Alliance, vol. 5, Issue 12, Aug. 1, 2022, pp. 1-16.
Ganesana, et al., "Site-specific Immobilization of a (His)6-Tagged Acetylcholinesterase on Nickel Nanoparticles for Highly Sensitive Toxicity Biosensors", In Journal of Biosensors and Bioelectronics, vol. 30, Issue 1, Dec. 15, 2011, pp. 43-48.
"Notice of Allowance Issued in U.S. Appl. No. 16/597,799", Mailed Date: Sep. 29, 2023, 9 Pages.
"Final Office Action Issued in U.S. Appl. No. 16/435,363", Mailed Date: Nov. 7, 2023, 16 Pages.
Non-Final Office Action mailed on Feb. 28, 2024, in U.S. Appl. No. 18/156,511, 14 pages.
U.S. Appl. No. 17/086,055, filed Oct. 30, 2020.
"Final Office Action Issued in U.S. Appl. No. 17/086,055", Mailed Date: Jul. 13, 2023, 13 Pages.
"Non-Final Office Action Issued in U.S. Appl. No. 17/815,380", Mailed Date: Dec. 1, 2023, 9 Pages.
Notice of Allowance mailed on Apr. 3, 2024, in U.S. Appl. No. 17/815,380, 9 pages.
Ashley, R, et al., Characterization of a Terminal Deoxynucleotidyl Transferase Activity in Mouse Mammary Tumor Virus, Department of Pathology, School of Medicine, and t Department of Bacteriology, College of Letters and Science, University of California, Davis, California 95616, Virology, 77, 367-375, 1977.
Namasivayam, V, et al., "Light-Induced Molecular Cutting: Localized Reaction on a Single DNA Molecule" Departments of Chemical Engineering, Human Genetics, and Electrical Engineering and Computer Science, The University of Michigan, Ann Arbor, Michigan 48109-2136 Anal. Chem., 75, Jan. 26, 2024, pp. 4188-4194.
Non-Final Office Action mailed on Feb. 1, 2024, in U.S. Appl. No. 17/086,055, 18 pages.
Corrected Notice of Allowability mailed on May 3, 2024, in U.S. Appl. No. 17/815,380, 7 pages.
Notice of Allowance mailed on May 30, 2024, in U.S. Appl. No. 17/695,734, 08 pages.
U.S. Appl. No. 17/494,320, filed Oct. 5, 2021.
U.S. Appl. No. 16/435,363, filed Jun. 7, 2019.
U.S. Appl. No. 16/597,799, filed Oct. 9, 2019.
Communication pursuant to Article 94(3) received in European Application No. 19842441.8, mailed on Oct. 16, 2024, 8 pages.
Communication pursuant to Article 94(3) Received in European Patent Application No. 20725319.6, mailed on Sep. 24, 2024, 4 pages.
Langston, Jennifer, "UW, Microsoft researchers break record for DNA data storage", Retrieved from the URL: https://www.washington.edu/news/2016/07/07/uw-microsoftresearchers-break-record-for-dna-data-storage/, Jul. 7, 2016, 5 Pages.
Communication pursuant to Article 94(3) Received in European Patent Application No. 20792779.9, mailed on Nov. 19, 2024, 4 pages.
Final Office Action issued in U.S. Appl. No. 17/086,055, mailed on Aug. 12, 2024, 14 Pages.
Notice of Allowance mailed on Aug. 19, 2024, in U.S. Appl. No. 18/156,511, 11 pages.
Wu et al., "Molecular hydrogelators of peptoid—peptide conjugates with superior stability against enzyme digestion" Nanoscale vol. 4, 2012, pp. 3644-3646.
Egeland, et al., "An Electrochemical Redox Couple Activated by Microelectrodes for Confined Chemical Patterning of Surfaces" Analytical Chemistry, vol. 74, 2002, pp. 1590-1596.
Final Office Action Issued in U.S. Appl. No. 16/563,797 Mailed Date: Jun. 27, 2022, 22 Pages.
Non-Final Office Action mailed on Dec. 12, 2024, in U.S. Appl. No. 17/494,320, 18 pages.
Non-Final Office Action mailed on Dec. 18, 2024, in U.S. Appl. No. 18/306,653, 08 pages.
Notice of Allowance mailed on Feb. 26, 2025, in U.S. Appl. No. 17/086,055, 5 Pages.
Notice of Allowance mailed on Jan. 8, 2025, in U.S. Appl. No. 17/086,055, 07 pages.
Notice of Allowance mailed on Jun. 16, 2023, in U.S. Appl. No. 16/563,797, 9 pages.
Unpublished U.S. Appl. No. 18/950,630 entitled "Selectively Controllable Cleavable Linkers," filed Nov. 18, 2024, 41 pages.
Dr. Joachim Engels, "Selektive elektrochemische Schutzgruppenabspaltung in der Nucleotidsynthese", Angewandte Chemie, vol. 91, Issue 2, Feb. 1979, pp. 155-156.
Hayakawa, et al., "Electrochemical Removal of Allylic Protecting Groups in Nucleotide Synthesis", Nucleosides and Nucleotides, vol. 17, Issue 1-3, 1998, pp. 441-449.
Notice of Allowance mailed on May 14, 2025, in U.S. Appl. No. 18/306,653, 9 pages.
Notice of Allowance mailed on May 20, 2025, in U.S. Appl. No. 17/494,320, 13 Pages.

* cited by examiner

REGULATION OF POLYMERASE USING COFACTOR OXIDATION STATES

CROSS-REFERENCE TO RELATED APPLICATION

This application is a division of, and claims priority to U.S. patent application Ser. No. 16/543,433, filed Aug. 16, 2019, the content of which is expressly incorporated herein by reference in its entirety.

BACKGROUND

Polynucleotides such as deoxyribose nucleic acid (DNA) are currently synthesized almost exclusively using a technique developed more than 35 years ago known as the nucleoside phosphoramidite method. The technique involves the sequential de-protection and synthesis of sequences built from phosphoramidite reagents corresponding to natural (or non-natural) nucleic acid bases. The nucleoside phosphoramidite method has been progressively refined over the years but is still limited to a maximum synthesis length of about 200-300 nucleotides. This technique also uses organic chemicals such as acetonitrile, trichloroacetic acid, toluene, tetrahydrofuran, and pyridine that create a toxic waste stream which is costly to dispose of and can have negative environmental impacts.

Recently, enzymatic polynucleotide synthesis has emerged as an alternate technique for the synthesis of polynucleotides. Enzymatic synthesis is performed in aqueous solutions without toxic or flammable chemicals and can generate longer polynucleotides than the nucleoside phosphoramidite method. However, one enzyme commonly used for enzymatic synthesis, terminal deoxynucleotide transferase (TdT), can be difficult to control because it adds any available nucleotide in an unregulated manner. Thus, it is more difficult with enzymatic synthesis to create a polynucleotide that has a specific and arbitrary sequence.

Enzymatic polynucleotide synthesis has advantages over the older nucleoside phosphoramidite method, but it is still a relatively new technique that will benefit from further refinements. This disclosure is made with respect to these and other considerations.

SUMMARY

This disclosure provides methods and devices for controlling enzymatic synthesis of polynucleotides by regulating the oxidation state of a metal cofactor. A cofactor is a non-protein chemical compound or metallic ion that is required for an enzyme's activity as a catalyst. DNA and ribonucleic acid (RNA) polymerases, including TdT, require a divalent metal cofactor cation to catalyze the polymerization of individual nucleotides into a polynucleotide. TdT uses an initiator polynucleotide sequence as a starting point for nucleotide polymerization. Absent the metal cofactor in the proper oxidation state of +2, polymerization will not occur at an appreciable rate even if all other necessary components are present. Regulation of the oxidation state of the metal cofactor is controlled by redox reactions initiated through electrodes or addition of chemical redox reagents. Spatial control of polymerization is provided by controlling the locations at which the metal cofactor in an oxidation state other than +2 (e.g., +0, +1, or +3) is oxidized or reduced to oxidation state of +2.

In an implementation, the techniques disclosed herein include delivering a reaction reagent solution which includes a template independent polymerase, a selected nucleotide, and metal cofactor in an oxidation state other than +2 oxidation state to a reaction site. The reaction site may include an array or other solid substrate. An initiator is attached to the reaction site and has a 3' terminal nucleotide. Polynucleotide synthesis is initiated by reducing or oxidizing the metal cofactor to the +2 oxidation state. This may be followed by delivering a wash solution that removes the reaction reagent solution which causes synthesis to stop.

In an implementation, this disclosure provides for an oligonucleotide synthesizer that is configured for oligonucleotide synthesis using a template independent polymerase. The oligonucleotide synthesizer includes an array covered with multiple initiators which each have a 3' terminal nucleotide. There is also a metal cofactor oxidation state control mechanism that can addressably oxidize or reduce metal cofactors at a selected location on the array. Spatial control of the metal cofactor oxidation state enables addressable activation of the template independent polymerase, and thus, spatial control of the locations on the array at which polynucleotide synthesis proceeds.

There are many possible techniques and devices that may be used as the metal cofactor oxidation state control mechanism. For example, the metal cofactor oxidation state control mechanism may be a microelectrode array with independently addressable electrodes, an inkjet printer capable of delivering small volumes of a redox reagent to precise locations on the array, or a light array capable of inducing a photoredox reaction by exciting a photocatalyst.

This Summary is provided to introduce a selection of concepts in a simplified form that are further described below in the Detailed Description. This Summary is not intended to identify key features or essential features of the claimed subject matter nor is it intended to be used to limit the scope of the claimed subject matter. The term "techniques," for instance, may refer to system(s) and/or method(s) as permitted by the context described above and throughout the document.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

This disclosure provides a method and device to control the activity of template independent polymerases by changing the oxidation state of the metal cofactor cation between divalent (+2) and another oxidation state (such as 0), +1, +3, etc.). The oxidation state of +2 allows for specific ligand coordination around the metal cofactor that other oxidation states do not allow: When the oxidation state is not +2, template independent polymerases cannot coordinate with the cation and the nucleotide polymerization reaction is stopped. Polymerase activity can be controlled by introducing the metal cofactor into a reaction site at an oxidation state other than the +2 oxidation state then changing the oxidation state of the metal cofactor to the +2 oxidation state. This change in metal cofactor oxidation state activates the template independent polymerases which begin polynucleotide synthesis.

Template independent polymerases are DNA or RNA polymerases that perform de novo oligonucleotide synthesis without use of a template strand. Currently known template independent polymerases include TdT and tRNA nucleotidyltransferase. TdT includes both the full-length wild-type enzyme, as well as modified enzymes that are truncated or internally modified. One example of modified TdT is provided in U.S. Pat. No. 10,059,929. An example of truncated TdT is provided in U.S. Pat. No. 7,494,797. Thus, template independent polymerase as used herein includes full-length wild-type, truncated, or otherwise modified TdT, tRNA nucleotidyltransferase, and any subsequently discovered or engineered polymerases that can perform template independent synthesis of polynucleotides. Template independent polymerase as used herein does not encompass modifications of TdT or tRNA nucleotidyltransferase that render those enzymes incapable of performing template independent nucleotide polymerization.

TdT is a protein that evolved to rapidly catalyze the linkage of naturally occurring deoxynucleotide triphosphates (dNTPs). TdT adds nucleotides indiscriminately to the 3' hydroxyl group at 3' end of single-stranded DNA. TdT performs unregulated synthesis adding any available dNTP. TdT uses an existing single-stranded polynucleotide referred to as an "initiator" as the starting point for synthesis. Initiators as short as three nucleotides have been successfully used with TdT for enzymatic synthesis of DNA. Suitable initiator length ranges from three nucleotides to about 30 nucleotides or longer. During the polymerization, the template independent polymerase holds a single-stranded DNA strand (which initially is only the initiator) and adds dNTPs in a 5'-3' direction. TdT activity is maximized at approximately 37° C. and performs enzymatic reactions in an aqueous environment.

Because TdT performs unregulated synthesis, using this enzyme to create a polynucleotide with a pre-specified arbitrary sequence requires regulation and control of the TdT activity. One technique to regulate TdT activity is limiting the available nucleotides to only a single type of dNTP or NTP (e.g., only dATP, dCTP, dGTP, dTTP, or UTP). Thus, providing only one choice forces the enzyme to add that type of nucleotide. However, this does not prevent the TdT from adding that nucleotide multiple times thereby creating homopolymers. Techniques for limiting homopolymer creation by TdT include using nucleotides with removable protecting groups, covalently coupling individual nucleotides to TdT enzymes, and limiting the available quantity of nucleotides. Examples of these techniques are briefly described below.

One technique for controlling enzymatic synthesis of oligonucleotides with TdT uses a modified TDT enzyme and dNTP analogs with protecting groups to prevent unregulated nucleotide addition. An example of this technique is described in U.S. Pat. No. 10,059,929. Techniques for enzymatic polynucleotide synthesis that use protecting groups typically flood a reaction tube with only one type of dNTP. The protecting group prevents polymerization so only a single nucleotide is added to the growing polynucleotide strand. Once coupling has taken place, the free dNTPs are washed away, the protecting group is removed with a deblocking solution, and the system is primed for the next round of single-nucleotide addition.

Another technique for enzymatic synthesis uses TdT enzymes each tethered to a single dNTP by a cleavable linker. See Sebastian Palluck et al., De novo *DNA synthesis using polymerase-nucleotide conjugates,* 36(7) Nature Biotechnology 645 (2018) and WO 2017/223517 A1. In this system, the TdT acts as its own protecting group preventing further chain elongation.

A third technique for nucleotide synthesis using TdT regulates activity of the polymerase by including the enzyme apyrase, which degrades nucleoside triphosphates into their TdT-inactive diphosphate and monophosphate precursors. See Henry H. Lee et al., *Terminator-free template-independent Enzymatic DNA Synthesis for Digital Information Storage,* 10:2383 Nat. Comm. (2019) and WO 2017/176541 A1. Apyrase limits polymerization by competing with TdT for nucleoside triphosphates.

There are many uses for synthetic polynucleotides having specified sequences such as basic research, medicine, and nanoengineering (e.g., DNA origami). One relatively recent application for synthetic polynucleotides is digital data storage. Polynucleotides such as DNA may be used to store digital information by designing a sequence of nucleotide bases—adenine (A), cytosine (C), guanine (G), and thymine (T)—that encodes the zeros and ones of the digital information. There are various techniques and encoding schemes known to those of skill in the art for using nucleotide bases to represent digital information. See Lee Organick et al., *Random Access in Large-Scale DNA Data Storage,* 36:3 Nat. Biotech. 243 (2018). Advantages of using DNA rather than another storage media for storing digital information include information density and longevity. The sequence of nucleotide bases is designed on a computer and then DNA molecules with that sequence are generated by an oligonucleotide synthesizer. The DNA may be stored and later read by polynucleotide sequencer to retrieve the digital information.

Oligonucleotides, also referred to as polynucleotides, include both deoxyribose nucleic acid (DNA), ribonucleic acid (RNA), and hybrids containing mixtures of DNA and RNA. DNA includes nucleotides with one of the four natural bases cytosine (C), guanine (G), adenine (A), or thymine (T) as well as unnatural bases, noncanonical bases, and/or modified bases. RNA includes nucleotides with one of the four natural bases cytosine, guanine, adenine, or uracil (U) as well as unnatural bases, noncanonical bases, and/or modified bases. Nucleotides include both deoxyribonucleotides and ribonucleotides covalently linked to one or more phosphate groups.

Figure 1:
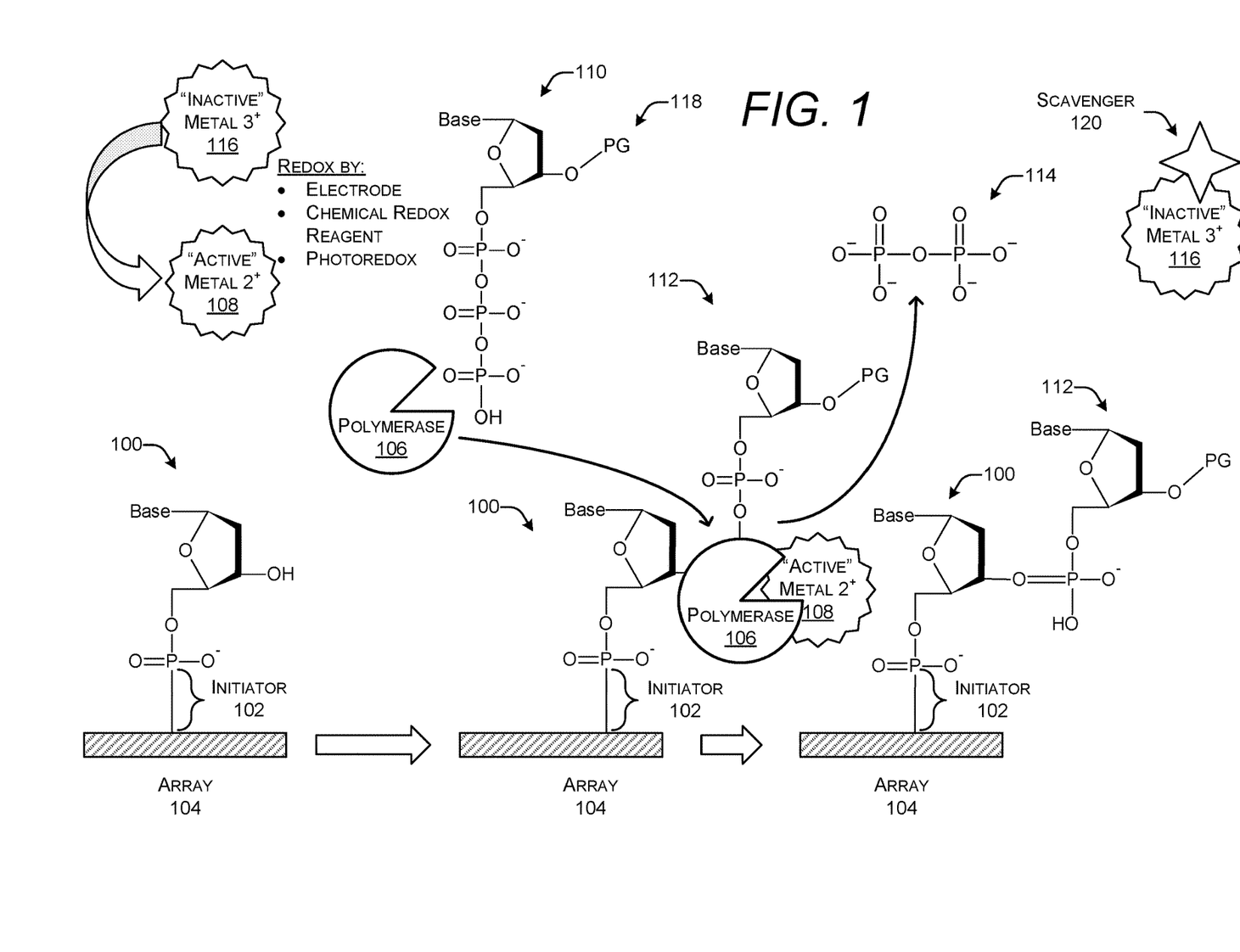
FIG. 1 is a diagram of polynucleotide synthesis on array in which activity of a polymerase is regulated by the oxidation state of a metal cofactor.

FIG. 1 shows an illustrative representation of enzymatic synthesis regulated by the oxidation state of a metal cofactor. Synthesis begins at a 3' terminal nucleotide 100 on the end of an initiator 102 that is attached to a solid support such as an array 104. The 3' terminal nucleotide 100 in this representation may be any deoxyribonucleotide or ribonucleotide with any canonical or noncanonical base. The initiator 102 is a single-stranded polynucleotide chain. The length of the initiator 102 may be about 3-30 nucleotides, about 15-25 nucleotides, or about 20 nucleotides. The initiator 102 is not shown to scale.

The initiator 102 is attached to the array 104 on some implementations another type of solid support such as a bead. The array 104 is an example of a solid support used for performing solid-phase polynucleotide synthesis. The array 104 may be formed from silicon dioxide, glass, an insoluble polymer, or other material. The initiator 102 may be attached to the array 104 using any known technique for anchoring single-stranded DNA or RNA to a solid support such as techniques used in conventional solid-phase synthesis of oligonucleotides or used for creation of DNA microarrays.

The array 104, or other solid support, is an example of is a platform used for solid-phase synthesis. Solid-phase synthesis is a method in which molecules are covalently bound on a solid support material and synthesized step-by-step in a single reaction vessel. Solid-phase synthesis may be used to make many types of polymers including, but not limited to, oligonucleotides.

The polymerase 106 is template independent polymerase such as TdT or tRNA nucleotidyltransferase. The polymerase 106 may be obtained from a number of sources such as isolation from calf thymus or from a recombinant source (e.g., a genetically modified $E.\ coli$ strain). The polymerase 106 and other entities that are not attached to the array 104 are present in aqueous solution (not shown) that covers the surface of the array 104. The aqueous solution may include buffers, salts, electrolytes, and the like.

The template independent polymerase TdT uses divalent metal cofactor cations for catalysis. TdT is able to use a variety of divalent metal cations such as $Co^{2+}$, $Mn^{2+}$, $Zn^{2+}$ and $Mg^{2+}$. The metal cofactors may be provided in the forms of salts such as $MgCl_2$ or $CoCl_2$. The salts form hydrates such as $MgCl_2\ (H_2O)$, or $CoCl_2 \cdot nH_2O$ (n=1,2,6, and 9) in aqueous solution. The divalent metal cation coordinates with TdT, or other polymerase 106, and the triphosphate of a dNTP 110 to catalyze the addition of a nucleotide to 3' terminal nucleotide 100 on the end of the initiator 102. This reaction creates a phosphodiester linkage between the nucleotide 112 of the dNTP 110 and the polynucleotide strand attached to the array 104 and releases pyrophosphate (PPi) 114.

The metal cofactor is any metal cofactor that both coordinates with the polymerase 106 to catalyze polymerization of nucleotides and that can be switched between at least two different oxidation states. A first oxidation state for the metal cofactor is referred to as an "active" oxidation state 108 in which the metal cofactor is a divalent metal cofactor cation with a +2 oxidation state. The +2 oxidation state is referred to as active because the polymerase 106 is able to actively catalyze nucleotide polymerization when the metal cofactor has this oxidation state. The second oxidation state is referred to as an "inactive" oxidation state 116. In this illustrative representation, the metal cofactor is shown as a trivalent cation with a +3 oxidation state as the inactive oxidation state 116. However, the inactive oxidation state 116 may be any oxidation state other than the +2 oxidation state such as 0 (solid metal), +1, +3, +4, etc. These oxidation states are referred to as inactive because the polymerase 106 does not coordinate with the metal cofactor when its oxidation state is not +2.

One suitable metal cofactor is cobalt. Cobalt can be provided as a cobalt complex such as a cobalt (III) complex or a cobalt (I) complex. Example cobalt complexes include trans-Dichlorobis (ethylenediamine) cobalt (III) chloride, pentaamminechlorocobalt (III) chloride, hexammine cobalt (III) chloride, trans-dichlorotetrakis(imidazole) cobalt (III) chloride or chlorotris(triphenylphosphine) cobalt (I). Synthesis of trans-Dichlorobis(ethylenediamine) cobalt (III) chloride, solubility in aqueous solutions, and reduction to cobalt (II) is described in Hart et al., *Synthesis and Characterization of trans-Dichlorotetrakis (imidazole) cobalt (III) Chloride: A New Cobalt (III) Coordination Complex with Potential Prodrug Properties*, Bioinorganic Chemistry and Applications, vol. 2018, Article ID 4560757, (2018).

The cobalt complex may be reduced or oxidized to cobalt (II) chloride ($CoCl_2$). For example, a Co(III)-complex can be reduced to a Co(II)-complex which can undergo ligand exchange with a buffered aqueous solution to form Co(II) which can then coordinate with TdT to "activate" it for polynucleotide synthesis. A ligand exchange reaction involves the substitution of one or more ligands in a complex ion with one or more different ligands.

Another suitable metal cofactor is magnesium. Magnesium may also be present as a magnesium salt such as magnesium chloride ($MgCl_2$). Magnesium may be provided as metallic magnesium, Mg(0), and can be oxidized by electrolysis at an anode in buffered solution to generate Mg(II). Reversing the current direction can reduce the Mg(II) to Mg(0). One technique for obtaining Mg(II) from a magnesium anode is described in Francis W. Ritchey et al., *Mg Anode Corrosion in Aqueous Electrolytes and Implications for Mg-Air Batteries*, 163(6) J. Electrochemical Soc'y, A958 (2016).

The metal cofactor is converted between the inactive oxidation state 116 and the active oxidation state 108 by a redox reaction. Redox, short for reduction-oxidation reaction, is a type of chemical reaction in which the oxidation states of atoms are changed. Redox reactions are characterized by the transfer of electrons between chemical species, most often with one species (the reducing agent) undergoing oxidation (losing electrons) while another species (the oxidizing agent) undergoes reduction (gains electrons). The chemical species from which the electron is stripped is said to have been oxidized, while the chemical species to which the electron is added is said to have been reduced.

The redox reaction may be initiated directly or indirectly at an electrode surface. At the electrode surface, reduction or oxidation would take place using electron transfer directly at the electrode or mediated by the redox of a mediator. Redox mediators are chemicals with electrochemical activity. In a bioelectrocatalysis process, mediators may exchange electrons with fuels or oxidants at the reaction sites of the biocatalysts, and then diffuse to the surface of electrode and exchange electrons there. Use of mediators may also reduce the required electrode potential which in turn reduces the energy needed to change the metal cofactor into the active oxidation state 108.

Chemical redox reagents may also be used to change the oxidation state of the metal cofactor between the inactive oxidation state 116 and the active oxidation state 108. The chemical redox reagents contribute or receive electrons from the metal cofactor in the inactive oxidation state 116 changing it to the active oxidation state 108 such as $Mg^{2+}$ or $Co^{2+}$. For example, ascorbic acid is a reducing agent that can reduce cobalt (III) to cobalt (II). Cobalt (II) may be oxidized to cobalt (III) by an amine (e.g., ammonia, ethylenediamine, ethylenediaminetetraacetic acid (EDTA), or tris(hydroxymethyl) aminomethane) in the presence of oxygen. The oxygen may be present as dissolved atmospheric oxygen in the aqueous solution or may be provided such as the addition of hydrogen peroxide.

In some implementations, the dNTP 110 may include a protecting group 118 (abbreviated in FIG. 1 as "PG") attached to the 3' hydroxyl group or to another location on the dNTP 110. Enzymatic synthesis can be performed using the techniques of the disclosure with or without a protecting group that prevents chain extension. The protecting group 118 may be any kind of moiety or group that prevents the polymerase 106 from extending the polynucleotide strand. Use of protecting groups may limit the addition of the nucleotides to one per cycle. As is known to those skilled in the art, there are various techniques for removing protecting groups 118 based on the specific composition of the protecting group 118 and the reaction environment. For example, a protecting group 118 may be removed by addition of chemicals (e.g., an acid or base solution), exposure to light, or exposure to heat.

Some examples of protecting groups 118 include esters, ethers, carbonitriles, phosphates, carbonates, carbamates, hydroxylamine, borates, nitrates, sugars, phosphoramide, phosphoramidates, phenylsulfenates, sulfates, sulfones, and amino acids. See Michael L. Metzker et al., *Termination of DNA Synthesis by Novel 3'-modified-deoxyribonucleoside 5'-triphosphates,* 22(20) Nucl. Acids Res., 4259(1994) and U.S. Pat. Nos. 5,763,594, 6,232,465, 7.414,116, and 7,279, 563. Other types of protecting groups 118 include 3'-O-amino, 3'-O-allyl, and a 3'-O-azidomethyl groups. Further examples of specific protecting groups 118 include O-phenoxyacetyl: O-methoxyacetyl: O-acetyl: O-(p-toluene)-sulfonate: O-phosphate: O-nitrate: O-[4-methoxy]-tetrahydrothiopyranyl: O-tetrahydrothiopyranyl: O-[5-methyl]-tetra-hydrofuranyl: O-[2-methyl,4-methoxy]-tetrahydropyranyl: O-[5-methyl]-tetrahydropyranyl; and O-tetrahydrothiofuranyl. See U.S. Pat. No. 8,133,669 for a discussion of these protecting groups. Additional examples of protecting groups are provided in U.S. patent application Ser. No. 16/230,787 filed on Dec. 21, 2018.

A scavenger 120 may also be present in the aqueous solution that covers the array 104. Scavengers 120 prevent diffusion of metal cofactors in a state that catalyzes activity of the template independent polymerase. For example, scavengers 120 may change the oxidation state of divalent metal cofactor cations to an inactive oxidation state 116. Scavengers 120 can be oxidizers such as an amine in the presence of oxygen. Scavengers 120 can be chelators such as EDTA and ethylenediamine that coordinate with and sequester metal cofactors without necessarily changing the oxidation state. The choice of scavenger 120 depends on the metal cofactor and persons of ordinary skill in the art can select appropriate scavengers 120 based on the type of metal cofactor and reaction conditions.

Figure 2:
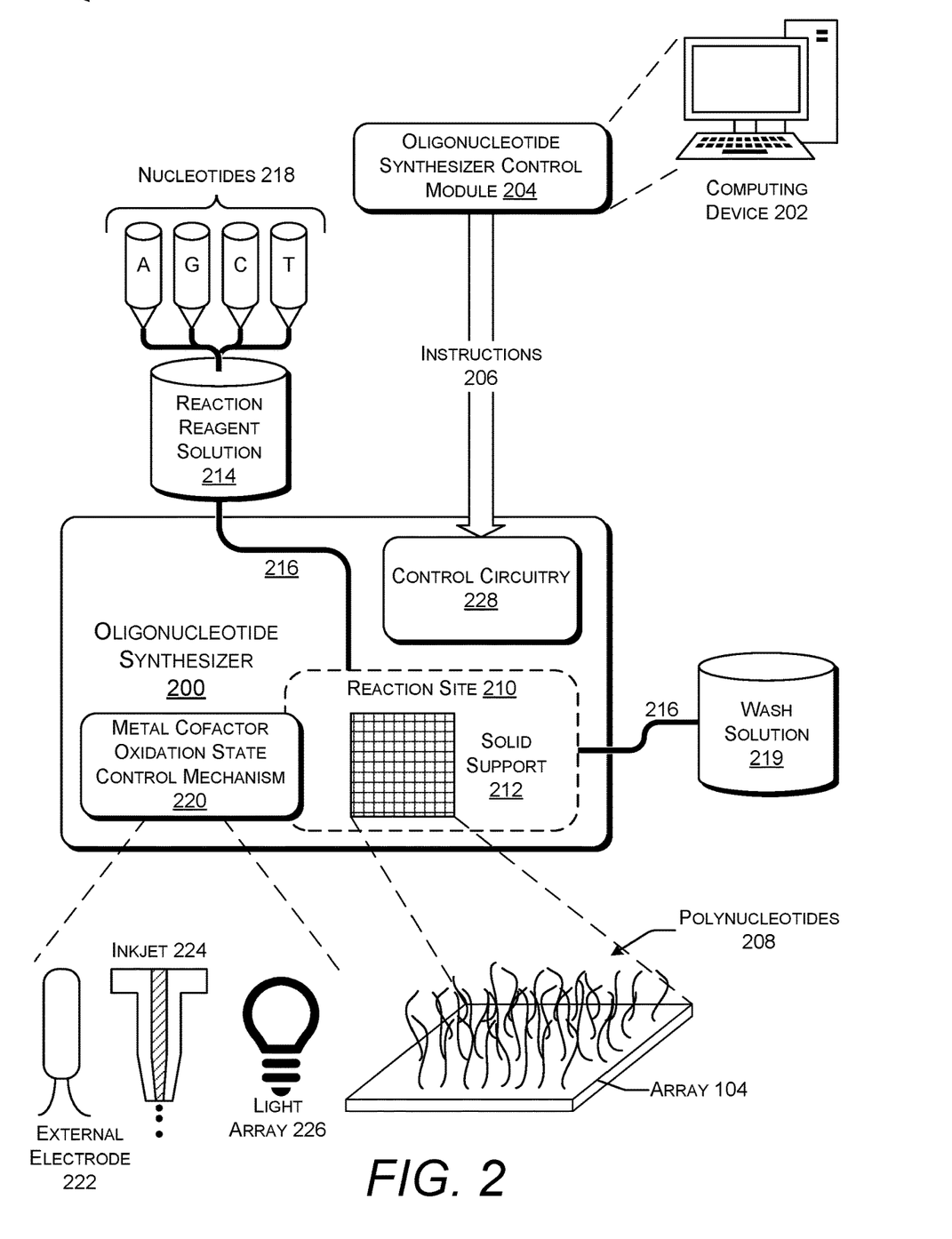
FIG. 2 is an architecture of a system for regulating synthesis of polynucleotides by controlling the oxidation state of a metal cofactor.

FIG. 2 shows an illustrative architecture of a system for implementing aspects of this disclosure. The system includes oligonucleotide synthesizer 200 and may also include a computing device 202. The computing device 202 includes an oligonucleotide synthesizer control module 204. The oligonucleotide synthesizer control module 204 provides instructions 206 that can control operation of the oligonucleotide synthesizer 200. For example, instructions 206 may communicate to the oligonucleotide synthesizer 200 base sequences of polynucleotides 208 for synthesis. The computing device 202 may be implemented as any type of conventional computing device such as a desktop computer, a laptop computer, a server, a hand-held device, or the like. In an implementation, the computing device 202 may be a part of the oligonucleotide synthesizer 200 rather than a separate device.

The oligonucleotide synthesizer 200 is a device that performs automated assembly of polynucleotides 208 at a reaction site 210 with a solid-phase process that assembles the polymers on a solid support 212. The reaction site 210 is the location at which nucleotide polymerization occurs and includes a chamber or container capable of maintaining an aqueous environment for the functioning of the template independent polymerase.

The solid support 212 may be a three-dimensional structure such as a bead or microsphere. Generally, the reaction site 210 will include a large number of identical or similar beads or microspheres in an aqueous solution. Beads and microspheres may be formed from silicon, glass, polystyrene, polymeric resins, latex, etc. The solid substrate may alternatively be a two-dimensional structure such as an array 104. The array 104 may be formed from silicon, glass, an insoluble polymer, or other material. One type of glass that may be used for a solid support 212 is controlled porous glass (CPG) with pore sizes between about 50 and 300 nm. The array 104 being a generally flat two-dimensional surface provides for addressable, site-specific manipulations at specified locations (e.g., represented in terms of x- and y-coordinates) on the surface of the array 104. The array 104 may be an electrochemically inert surface or it may include an array of spatially addressable microelectrodes.

A reaction reagent solution 214 may be delivered to the reaction site 210 through a fluid delivery pathway 216. The fluid delivery pathway 216 may be implemented by tubes and pumps, microfluidics, laboratory robotics, or other techniques. The reaction reagent solution 214 is an aqueous solution that contains the template independent polymerase, a selected nucleotide 218, a scavenger 120, and at least one of a salt, buffer, and a supporting electrolyte. The reaction reagent solution 214 may also include the metal cofactor in the inactive oxidation state 116. However, the metal cofactor in the inactive oxidation state 116 may also be provided as a solid metal that is not in solution.

If synthesizing DNA, for example, the selected nucleotide 218 may be a dNTP that includes one of natural bases adenine (A), guanine (G), cytosine (C), or thymine (T). Only one type of selected nucleotide is provided during each round of synthesis to control which nucleotide is next incorporated by the template independent polymerase into the polynucleotides 208. However, during different rounds of synthesis different ones of the available nucleotides may be used to create polynucleotides 208 with a specified nucleotide sequence.

The scavenger 120 restricts the location on the array 104 where the oxidation state of the metal cofactor is changed. A scavenger 120 prevents diffusion of the metal cofactor in a state that can catalyze activity of the template independent polymerase. The scavenger 120 may interact with divalent metal cofactor cations and change them to inactive oxidation states 116. The scavenger 120 may chelate metal cofactors and sequester the metal ions so that they are not able to interact with the template independent polymerase. Thus, even though the template independent polymerase may be present over the whole surface of the array 104, scavengers 120 limit the activity of the template independent polymerase to only those areas of the array 104 where the oxidation state of the metal cofactor has been changed to the active oxidation state 108.

The buffer may be any one of a number of aqueous buffers that are compatible with the template independent polymerase such as, for example, phosphate-buffered saline (PBS). PBS is a water-based salt solution containing disodium hydrogen phosphate, sodium chloride and, in some formulations, may also include one or more of potassium chloride and potassium dihydrogen phosphate. Other examples of aqueous buffers known to those of ordinary skill in the art include HEPES, MOPS, PBS, PBST, TAE, TBE, TBST, TE, and TEN. See Vincent S. Stoll & John S. Blanchard, *Buffers: Principles and Practice*, 182 Meth. Enzoml., 24(1990).

The supporting electrolyte may be included if electrodes are used to change the oxidation state of the metal cofactor. A supporting electrolyte, in electrochemistry, is an electrolyte containing chemical species that are not electroactive (within the range of potentials used) and which has an ionic strength and conductivity much larger than those due to the electroactive species added to the electrolyte. Supporting electrolytes are also referred to as inert electrolytes or inactive electrolytes. In some implementations, PBS functions as the supporting electrolyte. Other type of salt solutions used in aqueous buffers for biological reactions may also function as the supporting electrolyte.

A wash solution 219 may be added to the reaction site 210 as a step of the polynucleotide synthesis process. The wash solution 219 is water (e.g., DI (deionized) water) or an aqueous solution that contains at least one of a salt or a buffer. The salt or the buffer may be the same as the salt or buffer used in the reaction reagent solution 214. The wash solution 219 is flowed into the reaction site 210 through a fluid delivery pathway 216. The wash solution 219 is used to remove the reaction reagent solution 214 from the reaction site 210 so that a subsequent round of polymerization may occur with a different selected nucleotide 218. Displacing the reaction reagent solution 214 removes the template independent polymerase and is a way to stop synthesis of the polynucleotides 208.

The oligonucleotide synthesizer 200 also includes a metal cofactor oxidation state control mechanism 220 which changes the oxidation state of metal cofactors in the reaction site 210. Thus, the metal cofactor oxidation state control mechanism 220 changes conditions in all or part of the reaction site 210 such that metal cofactors in the inactive oxidation state 116 change to the active oxidation state 108. The metal cofactor oxidation state control mechanism 220 may also be used to stop template independent polymerase activity by changing the oxidation state of the metal cofactors from the active oxidation state 108 to the inactive oxidation state 116.

The metal cofactor oxidation state control mechanism 220 may be the array 104 implemented as an array of spatially addressable microelectrodes. The microelectrodes may be implemented with any known technology for creating microelectrodes such as complementary metal-oxide-semiconductor (CMOS) technology. CMOS may include metal-oxide-semiconductor field-effect transistors (MOSFETs) made through a triple-well process or by a silicon-on-insulator (SOI) process. A series of controllable gates/transistors implemented with CMOS circuits can be controlled to inject charge at any location on the surface of the array 104. Each spatially addressable microelectrode in the array 104 may be independently addressed allowing the creation of arbitrary and variable voltage microenvironments across the surface of the solid support 212.

High microelectrode density allows for fine-scale level control of the ionic environment at the surface of the array 104. A microelectrode array may have a microelectrode density of approximately 1024 microelectrodes/$cm^2$, approximately 12,544 microelectrodes/$cm^2$, or a different density. One example of a microelectrode array is provided in Bo Bi et al., *Building Addressable Libraries: The Use of "Safety-Catch" Linkers on Microelectrode Arrays*, 132 J. Am. Chem. Soc'y 17,405 (2010). One example of a microelectrode array and techniques for attaching polynucleotides to the surface of the array is provided in a Ryan D. Egeland & Edwin M. Southern, *Electrochemically Directed Synthesis of Oligonucleotides for DNA Microarray Fabrication*, 33(14) Nucleic Acids Res. e125 (2005).

Changes in the voltage microenvironments can result in reduction or oxidation of the metal cofactor thereby changing the oxidation state of the metal cofactor to the active oxidation state 108. Thus, the template independent polymerase has access to metal cofactors with a +2 oxidation state only where the microelectrodes are activated. Scavengers 120 present in the reaction reagent solution 214 prevent metal cofactors at other locations from changing to the active oxidation state 108. Thus, this provides for spatial control of the template independent polymerase activity so that the polynucleotides 208 are extended only at one or more selected locations on the array 104. Spatial control may also be implemented with a microelectrode array by reversing electrode polarity at regions of the array 104 other than the selected locations. The reversed polarity causes those electrodes to function as counter electrodes that prevent the metal cofactors in proximity to those electrodes from changing to the active oxidation state 108.

The voltage and current of individual electrodes in the array 104 are changed in reference to an external electrode 222. The external electrode 222 may be a counter electrode that is physically separate from the array 104. This is referred to as an "off-array" electrode. Alternatively, the external electrode 222 may be an "on-array" electrode that is part of the array 104. In some implementations, the metal cofactor oxidation state control mechanism 220 may include both an on-array electrode and one or more off-array electrodes such as in three electrode or four electrode systems. The working electrodes (not shown) or microelectrodes on the surface of the array 104 where the polynucleotides 208 are synthesized.

The external electrode 222 may be a source of the metal cofactor. The external electrode 222 may be made of a metal such as cobalt or magnesium that when oxidized releases a divalent metal cation into the solution in contact with the array 104. In this configuration, the voltage of the electrode may be set to the reduction potential of the metal. The metal cofactor may be present in the reaction site 210 simply as a metallic deposit rather than an electrode.

After a round of nucleotide extension is complete, the polarity of the external electrode 222 may be changed so that the metal cofactors in the +2 oxidation are reduced back to metallic form. The metal cofactors with an oxidation state of 0 may electroplate onto the external electrode 222 or other surface in the reaction site 210 and remain available for subsequent cycles of polymerization. Returning metal cofactor ions in solution to a solid metal phase prior to introducing the wash solution 219 into the reaction site 210 preserves the metal cofactors. The metal used to make the cofactors may then be reused or recycled. Reuse of the metal reduces the cost of polynucleotide synthesis. Reuse or recycling also keeps potentially hazardous metals out of the waste stream.

Alternatively, the metal cofactor oxidation state control mechanism 220 may be an inkjet printer 224 that is able to precisely apply small volumes of chemical redox reagent to specific locations on the surface of the array 104. Techniques for using inkjet printing to precisely deliver chemical reagents to selected locations on a surface of an array are well-known to those of ordinary skill in the art. In this implementation, the array 104 does not need to contain electrodes and may be an electrochemically inert surface. The chemical redox reagent delivered by the inkjet printer is a reducing reagent or oxidizing reagent that changes the oxidation state of the metal cofactor. For example, the chemical redox reagent may be ascorbic acid or an amine such as ammonia.

Another possible implementation of the metal cofactor oxidation state control mechanism 220 is a light array 226 that is capable of directing light to specific locations on the surface of the array 104. Light from the light array 226 excites a photocatalyst that performs a photoredox reaction with the metal cofactor or an intermediary. The light array 226 may include a photomask or digital micromirror device to direct the light. The light may be of any spectrum that is capable of initiating a photochemical reaction that does not damage polynucleotides or the template independent polymerase. In an implementation, the light array 226 generates visible light.

One suitable class of photoredox catalyst is the metal polypyridyl complexes of which iridium polypyridyl complexes are one example. These types of photoredox catalysts can perform single electron transfers (SET) as part of a series of reactions that reduce Co(III) to Co(II). See Megan H. Shaw et al., *Photoredox Catalysis in Organic Chemistry*, 81 J. Org. Chem. 6898 (2016).

The metal cofactor oxidation state control mechanism 220 may be controlled by control circuitry 228. The control circuitry 228 may be implemented as any type of circuitry suitable for controlling hardware devices such as a printed circuit board, microcontroller, a programmable logic controller (PLC), or the like. The control circuitry 228 receives the instructions 206 provided by the oligonucleotide synthesizer control module 204. The instructions 206 may indicate the regions of the array 104 at which polynucleotide synthesis will occur. The control circuitry 228 then causes the metal cofactor oxidation state control mechanism 220) to change the oxidation state of the metal cofactors to the active oxidation state 108 at the locations on the array 104 indicated by the instructions 206.

If the metal cofactor oxidation state control mechanism 220 is implemented as a microelectrode array, the control circuitry 228 is able to set the voltage independently at any (or all) of the electrodes in the array 104 in any arbitrary pattern. If the metal cofactor oxidation state control mechanism 220 is implemented as an inkjet printer 224, the control circuitry 228 may control the location of a print nozzle and the dispensing of a chemical redox reagent. Thus, the control circuitry 228 may cause a chemical redox reagent to be dispensed according to any arbitrary pattern across one or more selected locations on the array 104. For a light array 226, the control circuitry 228 controls the arrangement of a photomask or a digital micromirror devices that directs light only to specific regions of the array 104.

Figure 3:
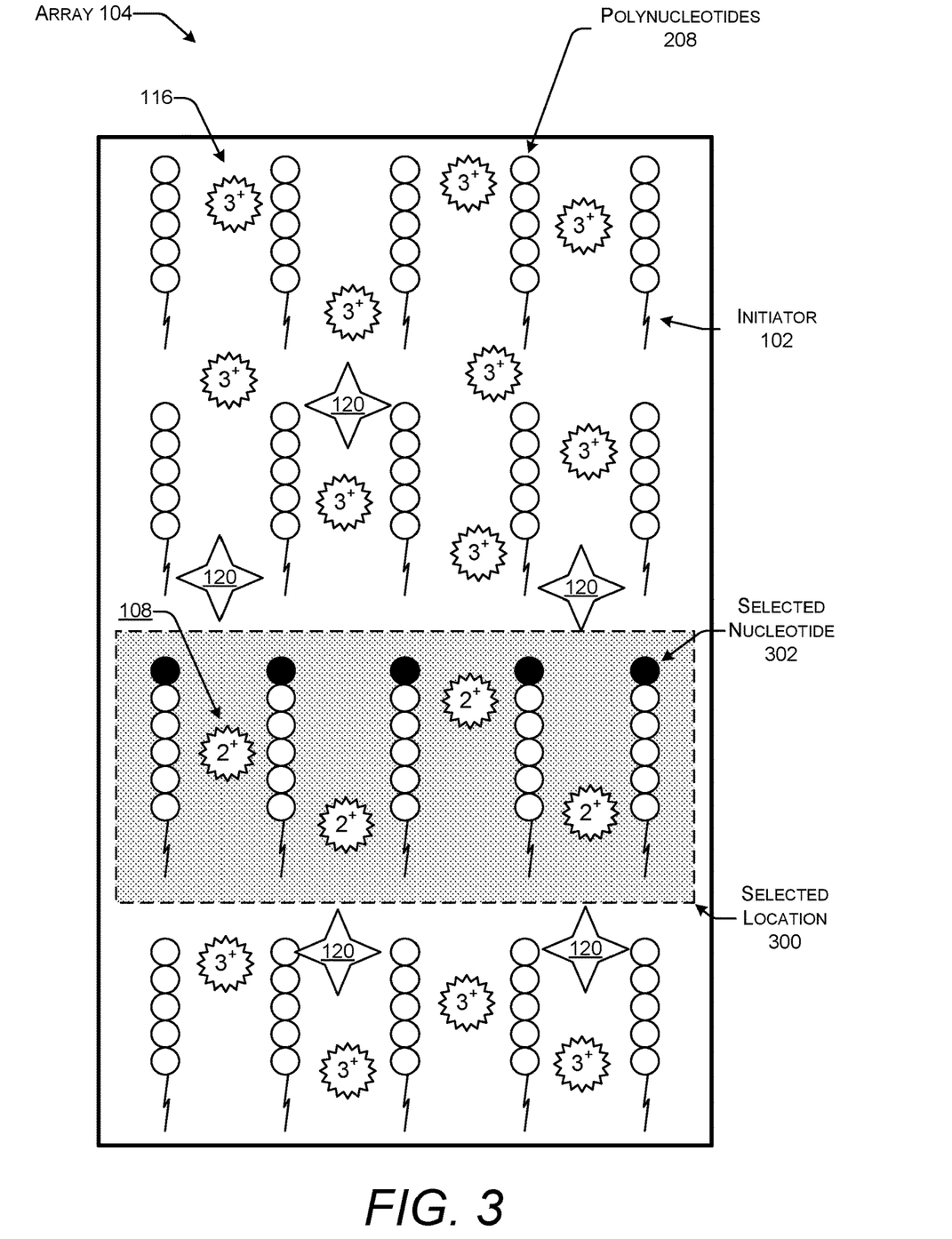
FIG. 3 shows an array with attached polynucleotides in which the oxidation state of a metal cofactor is of spatially controlled.

FIG. 3 shows a view of an array 104 covered with polynucleotides 208 illustrating spatial control of the oxidation state of a metal cofactor. The polynucleotides 208 each include an initiator 102 and a number of nucleotides added to the 3' end of the initiator 102. The initiator 102, not shown to scale, is represented as a thin line. Nucleotides added to the end of the initiator 102 are represented as circles.

Each of the initiators 102 attached to the array 104 may have the same nucleotide sequence or one or more of the initiators 102 may have different sequences. The sequence of any one or more of the initiators 102 may be a random sequence of nucleotides. The initiators 102 may be attached to the array 104 prior to enzymatic polynucleotide synthesis by any known technique for attaching single-stranded nucleotides to a solid support.

During polynucleotide synthesis, the surface of the array 104 is covered with an aqueous reaction reagent solution 214 that includes both a template independent polymerase and a metal cofactor in an oxidation state other than a +2 oxidation state (the inactive oxidation state 116). The representation of the metal cofactor in the inactive oxidation state 116 shows a charge of +3, but this is for illustrative purposes only and the metal cofactor in an inactive oxidation state may take any charge other than +2. Addressable control of the template independent polymerase is achieved by changing the oxidation state of the metal cofactor to the active oxidation state 108 only at a selected location 300 on the surface of the array 104.

Change of the oxidation state of the metal cofactor at the selected location 300 is implemented by the metal cofactor oxidation state control mechanism 220. Example implementations of the metal cofactor oxidation state control mechanism 220 are electrodes within the array 104, an inkjet printer 224 that delivers chemical redox reagents to the surface of the array 104, or a light array 226 that directs light to selectively excite photocatalysts. Application of the appropriate electric current, delivery of a chemical redox reagent, or excitation of a photocatalyst will directly or indirectly change the oxidation state of the metal cofactors at the selected location 300 to the active oxidation state 108. Metal cofactors with the active oxidation state 108 may be prevented from migrating outside of the selected location 300 by the presence of scavengers 120 that convert the oxidation state of the metal cofactors to the inactive oxidation state 116 or otherwise prevent the metal cofactors from catalyzing the template independent polymerase.

The selected location 300 may be any one or more locations that are contiguous or separate on the surface of the array 104. The resolution or minimum size of the selected location 300 is determined by the design of the metal cofactor oxidation state control mechanism 220. For example, the minimum size of the selected location 300 may be a single microelectrode which is determined by the density of spatially addressable electrodes (not shown) in the array 104. For an implementation that uses inkjet printing to deliver a chemical redox reagent, the minimum size of the selected location 300 may be determined by the minimum volume of liquid that can be delivered by the inkjet nozzle. The resolution a photomask or digital micromirror device used to direct light from a light array 226. The concentration, reductive/oxidative potential, and/or binding affinity of the scavenger 120 can also affect the size of the selected location 300.

The template independent polymerase is able to add a selected nucleotide 302 to the 3' end of the single-stranded polynucleotides 208 in the selected location 300. The selected nucleotide 302 may be the dNTP 110 shown in FIG. 1. The selected nucleotide 302 may be a one of the nucleotides 218 that is included in the reaction reagent solution 214. The selected nucleotide 302 may be present throughout the aqueous reagent reaction solution 214 across the entire surface of the array 104. However, the selected nucleotide 302 is incorporated into the polynucleotides 208 only at the selected location 300 where the metal cofactor is in the active oxidation state 108.

Due to the unregulated addition of nucleotides by template independent polymerases such as TdT, if the selected nucleotide 302 does not include a protecting group 118, more than one of the selected nucleotides 302 may be added. The number of nucleotides added to the polynucleotides 208 depends on the concentration of reagents and reaction conditions such as temperature and time. The length of time during which the template independent polymerase is able to add additional nucleotides onto the ends of the polynucleotides 208 may be limited by reversing the redox process. Doing so changes the metal cofactors at the selected location 300 from the active oxidation state 108 back to the inactive oxidation state 116. This will cease further activity of the template independent polymerase. Additionally, flooding the surface of the array 104 with the wash solution 219 will remove the template independent polymerase and free nucleotides which also stops polymerization.

Illustrative Process

For ease of understanding, the processes discussed in this disclosure are delineated as separate operations represented as independent blocks. However, these separately delineated operations should not be construed as necessarily order dependent in their performance. The order in which the processes are described is not intended to be construed as a limitation, and unless other otherwise contradicted by context any number of the described process blocks may be combined in any order to implement the process or an alternate process. Moreover, it is also possible that one or more of the provided operations is modified or omitted.

Figure 4:
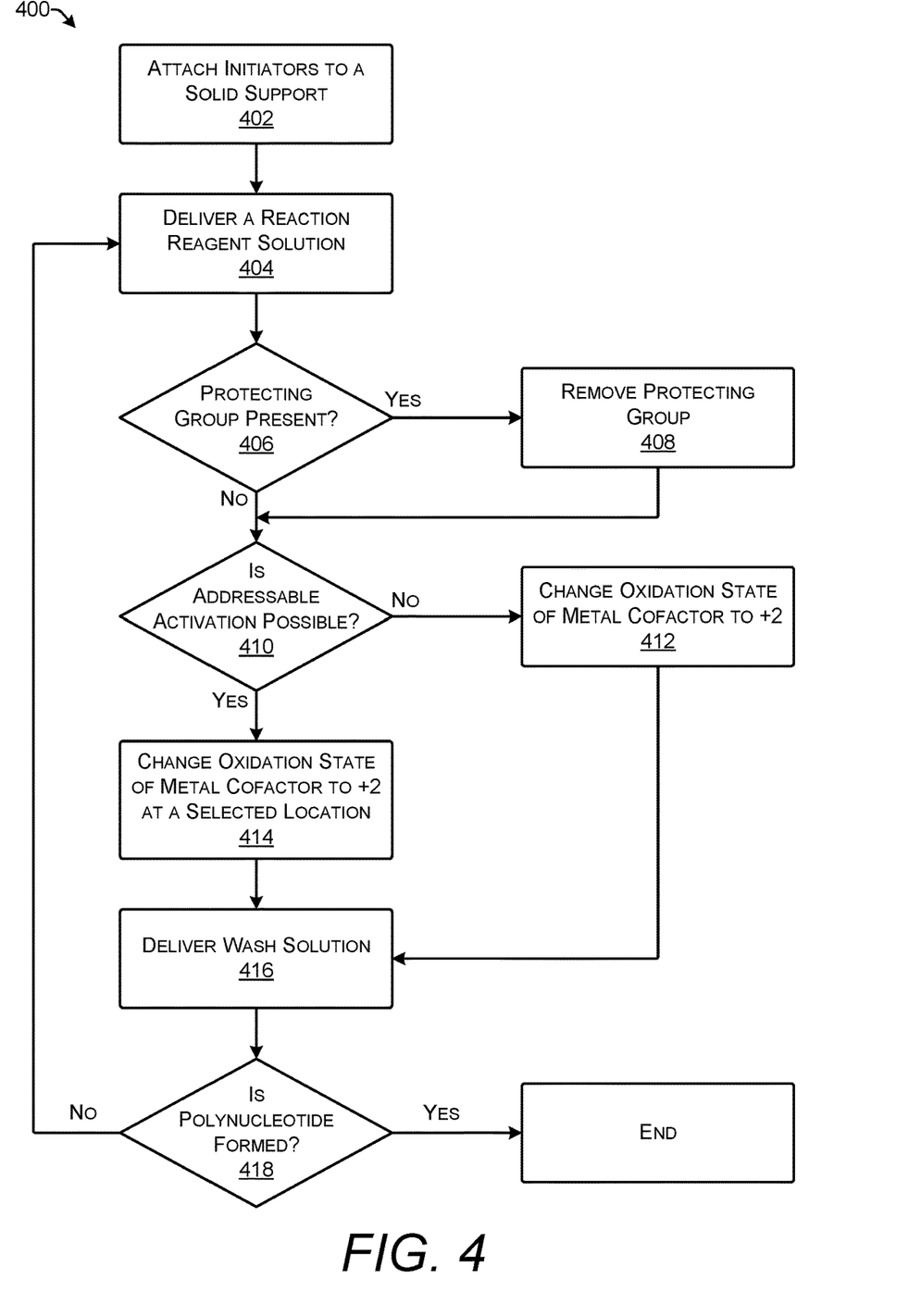
FIG. 4 is a flow diagram showing an illustrative process for controlling synthesis of polynucleotides by changing the oxidation state of a metal cofactor.

FIG. 4 shows process 400 for controlling synthesis of polynucleotides by changing the oxidation state of a metal cofactor. This process 400 may be implemented, for example, using any of the reactions, structures, and devices shown in FIGS. 1-3.

At 402, one or more initiators is attached to a solid support. The initiators are single-stranded nucleotides with a length of between about 3-30 bases. The template independent polymerase uses the initiators as a starting point for addition of additional nucleotides to the 3" terminal nucleotide at the end of each initiator. The solid support may be made out of silicon dioxide, glass, an insoluble polymer, or other material. The initiators may be attached to the solid support using any known technique for anchoring single-stranded DNA or RNA to a solid support such as techniques used in conventional solid-phase synthesis of oligonucleotides or used for creation of DNA microarrays.

Each of the initiators may be identical having the same length and nucleotide sequence. However, there may also be variation among the initiators in terms of length as well as sequence. In some implementations, the sequences of the initiators may include a cut site for restriction enzymes or other nucleases to cleave synthesized polynucleotides from the surface of the solid support.

The solid support that is coated with initiators may be a two-dimensional array or a three-dimensional structure such as a bead or microsphere. An array may be covered with many thousands or millions of separate initiators. In some implementations, many thousands or millions of beads or microspheres may be present in a single container such as an Eppendorf tube or column. The structure of the solid support does not directly affect the technique used for attaching initiators. However, the structure of the solid support may determine if specific locations on the solid support are addressable.

At 404, a reaction reagent solution is delivered to a reaction site. The reaction site includes the solid support prepared at 402. The reaction reagent solution may be delivered to the reaction site by a manual technique such as pipetting. The reaction reagent solution may also be delivered to the reaction site by automated or mechanized system such as via a fluid delivery pathway 216 as shown in FIG. 2.

The reaction reagent solution is an aqueous solution that contains the template independent polymerase, a selected nucleotide, a scavenger, and at least one of a salt, buffer, and a supporting electrolyte. For example, the template independent polymerase may be TdT. The reaction reagent solution may also include a metal cofactor in an oxidation state other than +2 oxidation state. For example, the metal cofactor may be cobalt (I) or cobalt (III). However, the metal cofactor in the oxidation state other than +2 oxidation state may also be provided as a solid metal that is not in solution. For example, metal cofactor may be metallic cobalt or metallic magnesium.

At 406, if a protecting group is present on the selected nucleotide, process 400 proceeds along the "yes" path to 408 and the protecting group is removed. The protecting group may be any kind of moiety or group that prevents the template independent polymerase from extending a polynucleotide strand. Some examples of protecting groups are esters, ethers, carbonitriles, phosphates, carbonates, carbamates, hydroxylamine, borates, nitrates, sugars, phosphoramide, phosphoramidates, phenylsulfenates, sulfates, sulfones, and amino acids.

At 408, the protecting group may be removed globally across the entire array or throughout the entire reaction site such as a plurality of beads in which spatial addressing is not possible. Removal of the protecting group may also be site-specific. The protecting group may be removed from the same selected location at which the oxidation state of the metal cofactor will be changed. However, it is not necessary for the area over which the protecting group is removed to be entirely congruent with the area of the array at which the oxidation state of the metal cofactor is changed. Yet, for synthesis to occur at a location, any protecting groups must be removed and the metal cofactor must be in the +2 oxidation state.

If a protecting group is not present, which is not necessary for some implementations of this technique, process 400 proceeds along "no" path to 410. At 410, process 400 proceeds differently if addressable activation of the metal cofactor is possible.

At 410, if addressable activation of the metal cofactor is not possible then process 400 proceeds along "no" path to 412. Addressable activation may be not be possible because the solid support is implemented as beads or microspheres. Even if the solid support is implemented as an array, addressable activation may not be possible if there is no mechanism for site-specific change of the metal cofactor oxidation state. If, however, addressable activation of the metal cofactor is possible such as, for example, through use of a microelectrode array, inkjet printer, or light array, process 400 proceeds along the "yes" path to 414.

At 412, the oxidation state of the metal cofactor is changed to +2 which is the active oxidation state. Depending on the previous oxidation state of the metal cofactor, this change may be implemented by reduction or oxidation. The reduction or oxidation may be implemented by applying an electrical current with an electrode or delivering a chemical redox reagent. In one example, a magnesium metal electrode is oxidixed by an electrical current and releases magnesium (II) into solution. In one example, the chemical redox reagent may be an amine in the presence of oxygen that oxidizes cobalt (I) to cobalt (II). In one example, the chemical redox reagent may be ascorbic acid that reduces cobalt (III) to cobalt (II).

In implementations where addressable activation is not possible, the change of the oxidation state of the metal cofactor occurs globally across all or substantially all of a reaction site. This change initiates polynucleotide synthesis by the template independent polymerase so that any nucleotides in solution are added to the 3' end of polynucleotides attached to the solid support.

At 414, if addressable activation is possible, the oxidation state of the metal cofactor is changed to +2 at a selected location. The metal cofactor at locations other than the selected location remains in the inactive oxidation state which is an oxidation state other than the +2 oxidation state. Addressable activation may be implemented by synthesizing the polynucleotides on a microelectrode array that includes a plurality of individually addressable electrodes. The metal cofactor is addressably reduced or oxidized by activating selected ones of the individually addressable electrodes at the selected location.

Addressable activation may also be implemented by reducing or oxidizing the metal cofactor with a redox reagent that is applied to selected locations on the array with inkjet printing. Selective excitation of a photocatalyst such as iridium polypyridyl by a light array can also be used to reduce or oxidize the metal cofactor. A photomask or digital micromirror device may direct light to only the selected locations on the array thus changing the metal cofactor to the +2 oxidation state only at the selected locations. In any implementation of addressable activation, the metal cofactor in the +2 oxidation state may be inhibited from spreading beyond the selected locations the by the presence of a scavenger. The scavenger may be a redox reagent that oxidizes or reduces the metal cofactor to an oxidation state other than the +2 oxidation state, a chelator that sequesters the metal cofactor, or a chemical that otherwise prevents the metal cofactor from catalyzing activity of the template independent polymerase. For example, the scavenger may be an amine in the presence of oxygen or EDTA.

At 416, a wash solution is delivered to the reaction site. The wash solution may be flowed across the entire reaction site displacing the reaction reagent solution and thereby stopping polymerization. The wash solution is water without added salts or an aqueous solution that contains at least one of a salt or a buffer. The buffer may be any one of a number of aqueous buffers that are compatible with polymerases and single-stranded nucleotides such as PBS.

At 418, is determined if the polynucleotide is formed. If all nucleotides needed to create the specified sequence of the polynucleotide have been added, then the polynucleotide is fully formed. Process 400 may then proceed along the "yes" path and end. If, however, the polynucleotide is not yet fully formed, process 400 proceeds along "no" path and returns to 404 where a reaction reagent solution is delivered to the reaction site. The reaction reagent solution in the subsequent iteration of synthesis may include a different selected nucleotide. A subsequent iteration may add nucleotides to a different set of polynucleotides on the array by changing the selected location used at 414.

This process may be repeated multiple iterations during synthesis of a polynucleotide. The sequence of nucleotide addition and the composition of the reaction reagent solution to deliver the selected nucleotide may be specified by the instructions 206 and implemented by the control circuitry 228 shown in FIG. 2. The selected location(s) at which synthesis is to proceed may also be specified by the instructions 206 and implemented by the control circuitry 228.

Illustrative Computer Architecture

Figure 5:
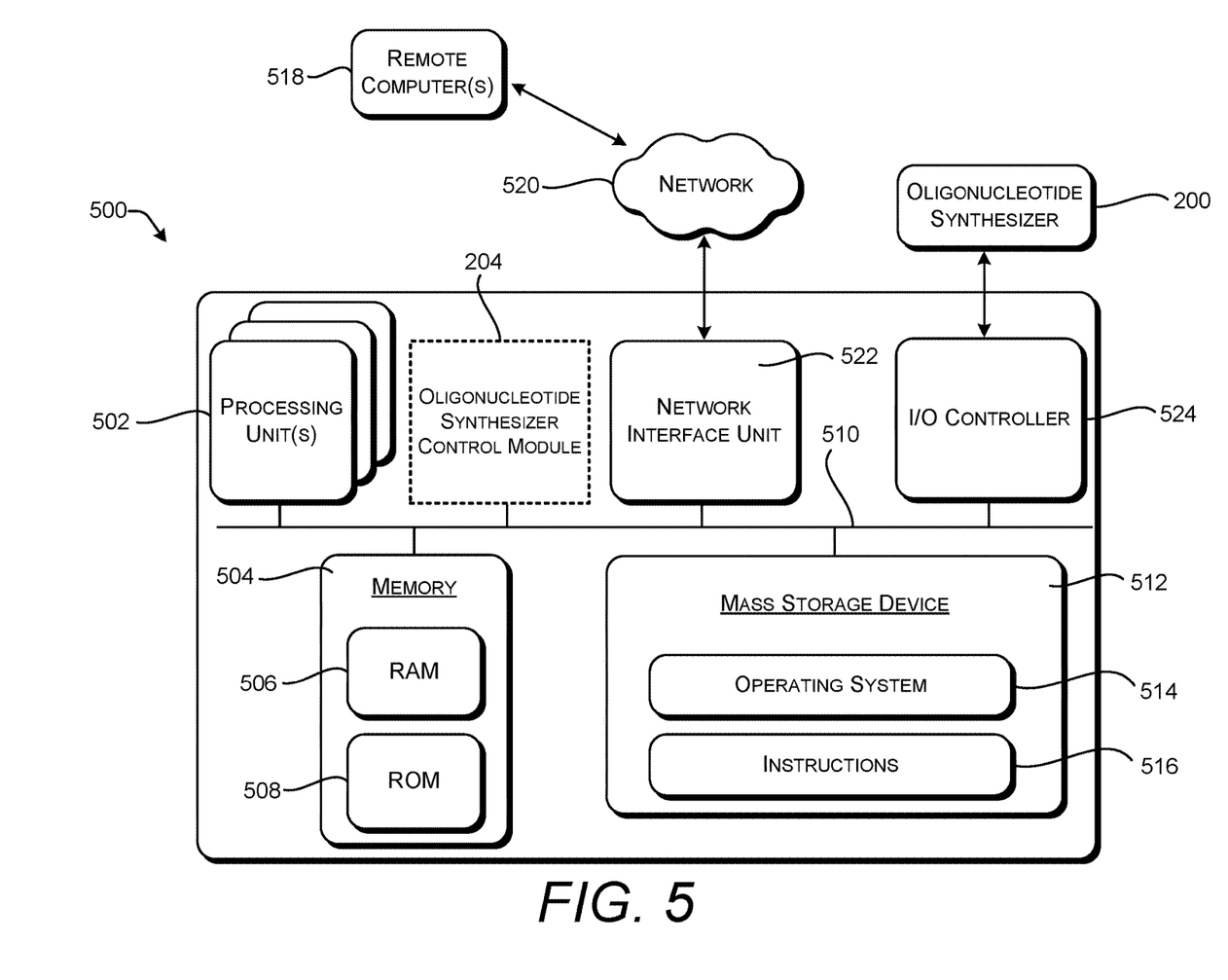
FIG. 5 is an illustrative computer architecture for implementing techniques of this disclosure.

FIG. 5 is a computer architecture diagram showing an illustrative computer hardware and software architecture for a computing device such as the computing device 202 introduced FIG. 2. In particular, the computer 500 illustrated in FIG. 5 can be utilized to implement the oligonucleotide synthesizer control module 204.

The computer 500 includes one or more processing units 502, a memory 504, that may include a random-access memory 506 ("RAM") and a read-only memory ("ROM") 508, and a system bus 510 that couples the memory 504 to the processing unit(s) 502. A basic input/output system ("BIOS" or "firmware") containing the basic routines that help to transfer information between elements within the computer 500, such as during startup, can be stored in the ROM 508. The computer 500 further includes a mass storage device 512 for storing an operating system 514 and other instructions 516 that represent application programs and/or other types of programs such as, for example, instructions to implement the oligonucleotide synthesizer control module 204. The mass storage device 512 can also be configured to store files, documents, and data such as, for example, sequence data that is provided to an oligonucleotide synthesizer 200 in the form of instructions 206.

The mass storage device 512 is connected to the processing unit(s) 502 through a mass storage controller (not shown) connected to the bus 510. The mass storage device 512 and its associated computer-readable media provide non-volatile storage for the computer 500. Although the description of computer-readable media contained herein refers to a mass storage device, such as a hard disk, solid-state drive, CD-ROM drive, DVD-ROM drive, or USB storage key, it should be appreciated by those skilled in the art that computer-readable media can be any available computer-readable storage media or communication media that can be accessed by the computer 500.

Communication media includes computer-readable instructions, data structures, program modules, or other data in a modulated data signal such as a carrier wave or other transport mechanism and includes any delivery media. The term "modulated data signal" means a signal that has one or more of its characteristics changed or set in a manner so as to encode information in the signal. By way of example, and not limitation, communication media includes wired media such as a wired network or direct-wired connection, and wireless media such as acoustic, radio frequency, infrared and other wireless media. Combinations of any of the above should also be included within the scope of computer-readable media.

By way of example, and not limitation, computer-readable storage media can include volatile and non-volatile, removable and non-removable media implemented in any method or technology for storage of information such as computer-readable instructions, data structures, program modules or other data. For example, computer-readable storage media includes, but is not limited to, RAM 506. ROM 508, EPROM. EEPROM, flash memory or other solid-state memory technology. CD-ROM, digital versatile disks ("DVD"). HD-DVD, BLU-RAY. 4K Ultra BLU-RAY, or other optical storage, magnetic cassettes, magnetic tape, magnetic disk storage or other magnetic storage devices, or any other medium that can be used to store the desired information and which can be accessed by the computer 500. For purposes of the claims, the phrase "computer-readable storage medium." and variations thereof, does not include waves or signals per se or communication media.

According to various configurations, the computer 500 can operate in a networked environment using logical connections to a remote computer(s) 518 through a network 520. The computer 500 can connect to the network 520 through a network interface unit 522 connected to the bus 510. It should be appreciated that the network interface unit 522 can also be utilized to connect to other types of networks and remote computer systems. The computer 500 can also include an input/output (I/O) controller 524 for receiving and processing input from a number of other devices, including a keyboard, mouse, touch input, an electronic stylus (not shown), or equipment such as an oligonucleotide synthesizer 200 or synthesizing polynucleotides according to the techniques of this disclosure. Similarly, the input/output controller 524 can provide output to a display screen or other type of output device (not shown).

It should be appreciated that the software components described herein, when loaded into the processing unit(s) 502 and executed, can transform the processing unit(s) 502 and the overall computer 500 from a general-purpose computing device into a special-purpose computing device customized to facilitate the functionality presented herein. The processing unit(s) 502 can be constructed from any number of transistors or other discrete circuit elements, which can individually or collectively assume any number of states. More specifically, the processing unit(s) 502 can operate as a finite-state machine, in response to executable instructions contained within the software modules disclosed herein. These computer-executable instructions can transform the processing unit(s) 502 by specifying how the processing unit(s) 502 transitions between states, thereby transforming the transistors or other discrete hardware elements constituting the processing unit(s) 502.

Encoding the software modules presented herein can also transform the physical structure of the computer-readable media presented herein. The specific transformation of physical structure depends on various factors, in different implementations of this description. Examples of such factors include, but are not limited to, the technology used to implement the computer-readable media, whether the computer-readable media is characterized as primary or secondary storage, and the like. For example, if the computer-readable media is implemented as semiconductor-based memory, the software disclosed herein can be encoded on the computer-readable media by transforming the physical state of the semiconductor memory. For instance, the software can transform the state of transistors, capacitors, or other discrete circuit elements constituting the semiconductor memory. The software can also transform the physical state of such components to store data thereupon.

As another example, the computer-readable media disclosed herein can be implemented using magnetic or optical technology. In such implementations, the software presented herein can transform the physical state of magnetic or optical media, when the software is encoded therein. These transformations can include altering the magnetic characteristics of particular locations within given magnetic media. These transformations can also include altering the physical features or characteristics of particular locations within given optical media, to change the optical characteristics of those locations. Other transformations of physical media are possible without departing from the scope and spirit of the present description, with the foregoing examples provided only to facilitate this discussion.

In light of the above, it should be appreciated that many types of physical transformations take place in the computer 500 to store and execute the software components presented herein. It also should be appreciated that the architecture shown in FIG. 5 for the computer 500, or a similar architecture, can be utilized to implement many types of computing devices such as desktop computers, notebook computers, servers, supercomputers, gaming devices, tablet computers, and other types of computing devices known to those skilled in the art. For example, the computer 500 may be wholly or partially integrated into the oligonucleotide synthesizer 200. It is also contemplated that the computer 500 might not include all of the components shown in FIG. 5, can include other components that are not explicitly shown in FIG. 5, or can utilize an architecture different than that shown in FIG. 5.

Illustrative Embodiments

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1 A method for synthesizing a polynucleotide comprising: (a) delivering a reaction reagent solution including a template independent polymerase, a selected nucleotide, and a metal cofactor in an oxidation state other than a +2 oxidation state to a reaction site that includes an initiator attached thereto, the initiator having a 3' terminal nucleotide; and (b) initiating polynucleotide synthesis by reducing or oxidizing the metal cofactor to the +2 oxidation state.

Clause 2. The method of clause 1, further comprising (c) delivering a wash solution to the reaction site to remove the reaction reagent solution.

Clause 3. The method of clause 2, further comprising iteratively repeating steps (a), (b), and (c) until the polynucleotide is formed.

Clause 4. The method of any one of clauses 1-3, further comprising stopping polynucleotide synthesis by reducing or oxidizing the metal cofactor to an oxidation state other than the +2 oxidation state.

Clause 5. The method of any one of clauses 1-4, wherein the template independent polymerase is terminal deoxynucleotide transferase (TdT).

Clause 6. The method of any one of clauses 1-5, wherein the selected nucleotide includes a protecting group and further comprising removing the protective group.

Clause 7. The method of any one of clauses 1-6, wherein the reducing or oxidizing the metal cofactor to the +2 oxidation state comprises one of applying an electrical current with an electrode, delivering a chemical redox reagent, or exciting a photocatalyist.

Clause 8. The method of clause 7, wherein the metal cofactor in an oxidation state other than +2 oxidation state is one of cobalt +1, cobalt +3, or magnesium metal.

Clause 9. The method of clause 8, wherein the reducing or oxidizing the metal cofactor to a +2 oxidation state comprises delivering a chemical redox reagent, wherein (i) the chemical redox reagent is an amine that oxidizes cobalt +1 to cobalt +2 or (ii) the chemical redox reagent is ascorbic acid that reduces cobalt +3 to cobalt +2.

Clause 10. The method of clause 7, wherein the reducing or oxidizing the metal cofactor to a +2 oxidation state comprises applying an electrical current with an electrode and the metal cofactor in an oxidation state other than +2 oxidation state is a magnesium metal electrode.

Clause 11. A method for synthesizing a plurality of polynucleotides having different sequences comprising: (a) delivering a reaction reagent solution including a template independent polymerase, a selected nucleotide, and metal cofactor in an oxidation state other than a +2 oxidation state to an array that is covered with a plurality of initiators attached thereto each having a 3' terminal nucleotide: (b) initiating polynucleotide synthesis at a selected location on the array by addressably reducing or oxidizing the metal cofactor to the +2 oxidation state at the selected location while the metal cofactor at an other location on the array remains in the oxidation state other than the +2 oxidation state: (c) delivering a wash solution to the array to remove the reaction reagent solution; and iteratively repeating steps (a), (b), and (c) such that the selected location changes at least once between iterations.

Clause 12. The method of clause 11, wherein the selected nucleotide includes a protecting group and further comprising removing the protecting group at the selected location.

Clause 13. The method of any one of clauses 11-12, wherein the array comprises a microelectrode array having a plurality of individually addressable electrodes and addressably reducing or oxidizing the metal cofactor comprises activating at least one of the individually addressable electrodes at the selected location.

Clause 14. The method of any one of clauses 11-12, wherein addressably reducing or oxidizing the metal cofactor comprises applying a chemical redox reagent to the selected location on the array by inkjet printing.

Clause 15. The method of any one of clauses 11-12, wherein addressably reducing or oxidizing the metal cofactor comprises exciting a photocatalyst at the selected locations with a light array.

Clause 16. The method of any one of clauses 11-15, wherein reaction reagent solution further includes a scavenger that is a chemical redox reagent which oxidizes or reduces the metal cofactor to an oxidation state other than the +2 oxidation state or a chelator.

Clause 17. The method of clause 16, wherein the scavenger is one of an amine or EDTA.

Clause 18. An oligonucleotide synthesizer configured for polynucleotide synthesis using a template independent polymerase comprising: an array covered with a plurality of initiators attached thereto each having a 3' terminal nucleotide: a metal cofactor oxidation state control mechanism that addressably oxidizes or reduces a metal cofactor at a selected location on the array; and control circuitry communicatively coupled to the metal cofactor oxidation state control mechanism and configured to selectively activate the metal cofactor oxidation state control mechanism at the selected location on the array.

Clause 19. The oligonucleotide synthesizer of clause 18, further comprising a reaction reagent solution in contact with the array and comprising the template independent polymerase, a selected nucleotide, and the metal cofactor in an oxidation state other than a +2 oxidation state.

Clause 20. The oligonucleotide synthesizer of clause 19, wherein the reaction reagent solution further comprises a scavenger that is a redox reagent which oxidizes or reduces the metal cofactor to an oxidation state other than the +2 oxidation state or a chelator.

Clause 21. The oligonucleotide synthesizer of any one of clauses 18-20, wherein the plurality of initiators may be the same or different from each other and individual ones of the plurality of initiators are polynucleotide sequences of 3-30 nucleotides.

Clause 22. The oligonucleotide synthesizer of any one of clauses 18-21 wherein the array comprises glass, silicon, or an insoluble polymer.

Clause 23. The oligonucleotide synthesizer of any one of clauses 18-21, wherein the array is a microelectrode array including spatially addressable electrodes and the metal cofactor oxidation state control mechanism is the microelectrode array.

Clause 24. The oligonucleotide synthesizer of clause 23, wherein the microelectrode array includes a Mg(0) metal electrode.

Clause 25. The oligonucleotide synthesizer of any one of clauses 18-22, wherein the metal cofactor oxidation state control mechanism is an inkjet printer configured to deliver a chemical redox reagent to the selected location on the array.

Clause 26. The oligonucleotide synthesizer of any one of clauses 18-22, wherein the metal cofactor oxidation state control mechanism is a light array configured to direct light to photocatalysts at the selected locations on the array.

CONCLUSION

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

The terms "a," "an," "the" and similar referents used in the context of describing the invention are to be construed to cover both the singular and the plural unless otherwise indicated herein or clearly contradicted by context. The terms "based on," "based upon," and similar referents are to be construed as meaning "based at least in part" which includes being "based in part" and "based in whole," unless otherwise indicated or clearly contradicted by context. The terms "portion," "part," or similar referents are to be construed as meaning at least a portion or part of the whole including up to the entire noun referenced. As used herein, "approximately" or "about" or similar referents denote a range of +10% of the stated value.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Furthermore, references have been made to publications, patents, and/or patent applications throughout this specification. Each of the cited references is individually incorporated herein by reference for its particular cited teachings as well as for all that it discloses.

The invention claimed is:

1. An oligonucleotide synthesizer configured for polynucleotide synthesis using a template independent polymerase comprising:
   an array covered with a plurality of initiators attached thereto each having a 3' terminal nucleotide;
   a solid metal source;
   a metal cofactor oxidation state control mechanism that addressably oxidizes the solid metal source at a selected location on the array to release a metal cofactor in a +2 oxidation state;
   control circuitry communicatively coupled to the metal cofactor oxidation state control mechanism and configured to selectively activate the metal cofactor oxidation state control mechanism at the selected location on the array; and
   a reaction reagent solution in contact with the array and comprising the template independent polymerase and a selected nucleotide, wherein the reaction reagent solution further comprises a scavenger that is a redox reagent which oxidizes or reduces the metal cofactor to an oxidation state other than the +2 oxidation state or a chelator.

2. The oligonucleotide synthesizer of claim 1, wherein the plurality of initiators may be the same or different from each other and individual ones of the plurality of initiators are polynucleotide sequences of 3-30 nucleotides.

3. The oligonucleotide synthesizer of claim 1, wherein the solid metal source is a metallic deposit.

4. The oligonucleotide synthesizer of claim 1, wherein the solid metal source is metallic cobalt or metallic magnesium.

5. The oligonucleotide synthesizer of claim 1, wherein the solid metal source is an external electrode of the array and the external electrode is an on-array electrode.

6. The oligonucleotide synthesizer of claim 5, wherein reduction of the metal cofactor in the +2 oxidation state back to metallic form causes electroplating of the external electrode.

7. The oligonucleotide synthesizer of claim 1, further comprising an off-array electrode that is a counter electrode physically separate from the array as part of a three or four electrode system.

8. An oligonucleotide synthesizer configured for polynucleotide synthesis using a template independent polymerase comprising:
   an array covered with a plurality of initiators attached thereto each having a 3' terminal nucleotide;
   a solid metal source;
   a metal cofactor oxidation state control mechanism that oxidizes the solid metal source on the array to release a metal cofactor in a +2 oxidation state;
   control circuitry communicatively coupled to the metal cofactor oxidation state control mechanism and configured to selectively activate the metal cofactor oxidation state control mechanism on the array; and
   a reaction reagent solution in contact with the array and comprising the template independent polymerase, a selected nucleotide, and a chelator.

9. The oligonucleotide synthesizer of claim 8, wherein the plurality of initiators may be the same or different from each other and individual ones of the plurality of initiators are polynucleotide sequences of 3-30 nucleotides.

10. The oligonucleotide synthesizer of claim 8, wherein the solid metal source is a metallic deposit.

11. The oligonucleotide synthesizer of claim 8, wherein the solid metal source is metallic cobalt or metallic magnesium.

12. The oligonucleotide synthesizer of claim 8, wherein the solid metal source is an external electrode of the array and the external electrode is an on-array electrode.

13. The oligonucleotide synthesizer claim 12, wherein reduction of the metal cofactor in the +2 oxidation state back to metallic form causes electroplating of the external electrode.

14. An oligonucleotide synthesizer configured for polynucleotide synthesis using a template independent polymerase comprising:
   a microelectrode array including spatially addressable electrodes, the microelectrode array covered with a plurality of initiators attached thereto each having a 3' terminal nucleotide;
   a solid metal source;
   control circuitry communicatively coupled to the microelectrode array and configured to oxidize the solid metal source to release a metal cofactor in a +2 oxidation state; and
   a reaction reagent solution in contact with the microelectrode array and comprising the template independent polymerase, a selected nucleotide, and a scavenger that is a redox reagent which oxidizes or reduces the metal cofactor to an oxidation state other than the +2 oxidation state or a chelator.

15. The oligonucleotide synthesizer of claim 14, wherein the solid metal source is an external electrode of the microelectrode array.

16. The oligonucleotide synthesizer of claim 15, wherein reduction of the metal cofactor in the +2 oxidation state back to metallic form causes electroplating of the external electrode.

17. The oligonucleotide synthesizer of claim 14, wherein the solid metal source is a metallic deposit.

18. The oligonucleotide synthesizer of claim 14, wherein the plurality of initiators may be the same or different from each other and individual ones of the plurality of initiators are polynucleotide sequences of 3-30 nucleotides.

19. The oligonucleotide synthesizer of claim 14, wherein the solid metal source is metallic cobalt or metallic magnesium.

20. The oligonucleotide synthesizer of claim 14, further comprising an off-array electrode that is a counter electrode physically separate from the array as part of a three or four electrode system.

* * * * *